US010635702B2

(12) United States Patent
Dow et al.

(10) Patent No.: US 10,635,702 B2
(45) Date of Patent: Apr. 28, 2020

(54) INFERRING ECOLOGICAL NICHE MODEL INPUT LAYERS AND PREDICTING A FUTURE GEOSPATIAL LOCATION OF A SPECIES

(71) Applicant: International Business Machines Corporation, Armonk, NY (US)

(72) Inventors: Eli M. Dow, Wappingers Falls, NY (US); Matthew M. Klawonn, Troy, NY (US); Harry R. Kolar, Scottsdale, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 510 days.

(21) Appl. No.: 15/379,896

(22) Filed: Dec. 15, 2016

(65) Prior Publication Data

US 2018/0173820 A1    Jun. 21, 2018

(51) Int. Cl.
*G06F 16/35* (2019.01)
*G16B 99/00* (2019.01)
*G06N 20/00* (2019.01)

(52) U.S. Cl.
CPC ............. *G06F 16/35* (2019.01); *G16B 99/00* (2019.02); *G06N 20/00* (2019.01)

(58) Field of Classification Search
None
See application file for complete search history.

(56) References Cited

U.S. PATENT DOCUMENTS

| 8,291,069 | B1 | 10/2012 | Phillips |
| 8,321,503 | B2 | 11/2012 | Endres et al. |
| 2003/0023416 | A1 | 1/2003 | Peterson |
| 2006/0265197 | A1 | 11/2006 | Peterson |
| 2012/0253790 | A1 | 10/2012 | Heck et al. |
| 2014/0189598 | A1 | 7/2014 | Barros |
| 2015/0332622 | A1 | 11/2015 | Liu et al. |
| 2015/0341653 | A1 | 11/2015 | Ostrovskiy et al. |
| 2015/0356083 | A1 | 12/2015 | Gyongyi et al. |

OTHER PUBLICATIONS

Bolchini, et al., "A Data-Oriented Survey of Context Models", ACM SIGMOD Record, vol. 36, No. 4, 2007, 8 pages.
Michael, J., Marioj, et al. "Causal Diagrams in Systems Epidemiology", Emerging Themes in Epidemiology. doi: 10.1186/1742-7622-9-1, 2012, 13 pages.
List of IBM Patents or Patent Applictions Treated As Related; (Appendix P), Filed Dec. 15, 2016, 2 pages.
Anonymously; "Collaborative Annotation Enhancement"; http://ip.com/IPCOM/000223756D; Nov. 28, 2012, 5 pages.
Anonymously; "Fine-Grained Type-Activated Hierarchical Analytic Engine"; http://ip.com/IPCOM/000236357D; Apr. 22, 2014, 4 pages.
Anonymously; "Method of tracing document content changing and synchronizing the reference document based on annotation in content manager system";http://ip.com/IPCOM/000232515D; Nov. 15, 2013, 18 pages.
Anonymously; "Simultaneous Expert, Project, and Document Search Using Knowledge Graph"; http://ip.com/IPCOM/000242152D; Jun. 19, 2015 7 pages.

*Primary Examiner* — G Steven Vanni
(74) *Attorney, Agent, or Firm* — Cantor Colburn LLP; Teddi Maranzano

(57) ABSTRACT

An aspect includes aggregating a plurality of disparate datasets into a document store with semi-structured attributes that includes a plurality of documents specifying a plurality of different geo spatial locations and a plurality of different environmental parameters. Niche model layers are generated for the environmental parameters at the geospatial locations based on contents of the document store. The niche model layers include a model layer for each of the different environmental parameters. An additional niche model layer is created for a derived environmental parameter at the geospatial locations based at least in part on one of the previously generated niche model layers. A future geospatial location of a species is predicted based on environmental attributes of the species and contents of at least a subset of the niche model layers. The predicted future geospatial location of the species overlaid on a geographic map is output.

20 Claims, 6 Drawing Sheets

INFERRING ECOLOGICAL NICHE MODEL INPUT LAYERS AND PREDICTING A FUTURE GEOSPATIAL LOCATION OF A SPECIES

BACKGROUND

The present invention relates to ecological niche modeling, and more specifically, to inferring ecological niche model input layers from other model input layers.

Ecological niche modeling (ENM) refers to the process of using computer algorithms to predict the distribution of species (e.g., plants, animals, or other living organisms) in geographic space on the basis of a mathematical representation of their known distribution in environmental space. The environment in most cases is represented as climate data (such as temperature and precipitation), however other variables such as soil type, water depth, and land cover can also be used. These models allow for interpolating between a limited number of species' occurrences and are useful in research areas related to conservation biology, ecology, and evolution.

There are a number of motivations for using ENM to understand the range of environmental conditions suitable for a species' survival in the absence of inter-species interactions given a set of environmental parameters. A nascent application of ENM is the projection of species' distributions under climate change scenarios. An understanding of critical species' fundamental niches allows forecasters to predict changes in populations as climate shifts. Another use of ENM is in the prediction of invasive species' habitats in "un-invaded" regions. Invasive species can cause significant damage to the ecosystems that they invade, and thus in turn can have harmful impacts on the humans who rely on those ecosystems. Understanding the fundamental niches of invasive species allows for identification of at risk locations, and can potentially limit the search space for entities interested in seeking out their locations in non-native ecosystems.

SUMMARY

Embodiments include a method, system, and computer program product for ecological niche modeling. A method includes aggregating a plurality of disparate datasets into a document store with semi-structured attributes, each document in the document store specifying a geospatial location and a value of an environmental parameter at the geospatial location. The document store includes a plurality of documents specifying a plurality of different geospatial locations and a plurality of different environmental parameters. The environmental parameters include a climatological parameter. Niche model layers are generated for the environmental parameters at the geospatial locations based on contents of the document store. The niche model layers include a model layer for each of the different environmental parameters. An additional niche model layer is created for a derived environmental parameter at the geospatial locations based at least in part on one of the previously generated niche model layers. A future geospatial location of a species is predicted based on environmental attributes of the species and contents of at least a subset of the niche model layers. The subset includes the additional niche model layer. The predicted future geospatial location of the species overlaid on a geographic map is output.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
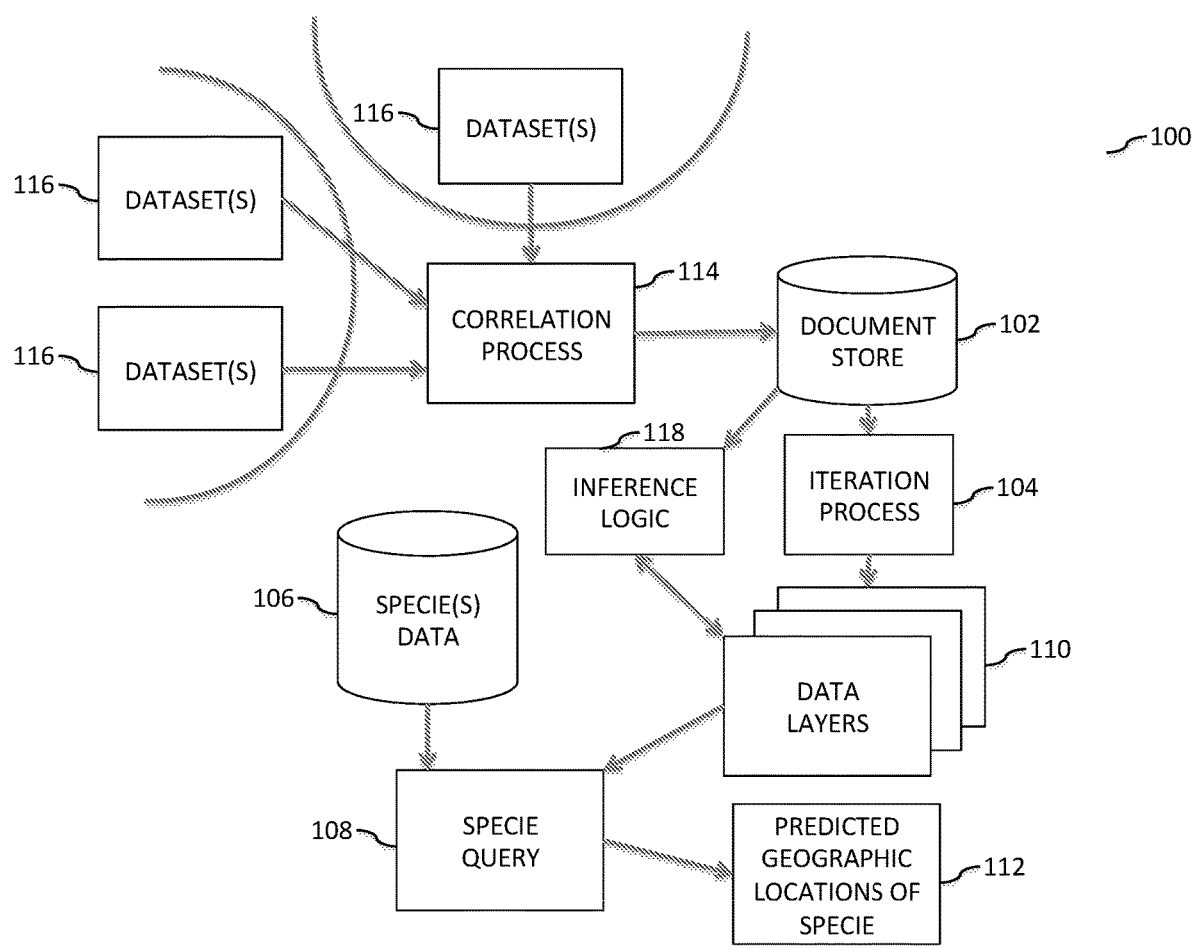
FIG. 1 illustrates components of a flexible ecological niche modeling (ENM) framework in accordance with one or more embodiments.

Embodiments described herein include a framework for providing ecological niche modeling (ENM). In accordance with one or more embodiments, a user inputs the names of a geographic region and species into the ENM in order to predict possible future locations of the species in the geographic region. Geospatial referenced gridded datasets can be indexed into annotated document structures and stored in a document store of an enterprise search platform. In one or more embodiments, the enterprise search platform is implemented using Apache Solr from the Apache Software Foundation. Using the enterprise search platform, a set of shapes, ways, or regions (effectively nested levels of locations which are defined hierarchically) can be indexed, and the document store can be used to retrieve data values and metadata limited in scope to a user specified region. The retrieved data values and metadata, also referred to herein as data layers, can be used in combination with information about environmental preferences of a species to predict possible future geographic locations of the species.

In one or more embodiments, data in the document store can be used to autonomously derive new data layers for ENM, which can improve the accuracy of the models. For example, a new data layer can be generated that includes the locations of a food source (e.g., an animal, a plant) of a species. This can be derived via a combination of a graph database query seeking all known food sources of a species of interest, and then querying, for each food species, a presence dataset (which is typically only used in reference to the species of interest) to determine geographic locations of the food species.

In one or more embodiments, additional data layers are inferred based on contents of the one or more of the data layers which may also be combined with additional data. In accordance with one or more embodiments, the inferring includes performing calculations on the data in one or more data layers to generate a new data layer. One example of an inferred data layer is an amount of hours of sun/shade per day at a geographic location. In this example, an amount of sun/shade at a geographic location can be inferred based on an elevation of the geographic location and neighboring geographic locations, and a position of the sun.

One or more embodiments of the framework for ENM described herein provide data persistence and flexible data access, coupled with a clear presentation of results and fine-tuned control over model parameters. Massive amounts of data (e.g., over a terabyte) measuring environmental parameters such as, but not limited to: weather related phenomena, land cover, soil type, population, species occurrence, general species information, and elevation can be leveraged. In addition, high-resolution spatial data can also be utilized to provide more accurate models. One or more embodiments store data in an instance of Apache Solr layers and thus, layers that are generated in support of niche models are accessible to users via simplified Apache Lucene queries. User access can be simplified further by using a Hypertext Transfer Protocol (HTTP) front end that generates Apache Lucene queries automatically. In one or more embodiments, a user need only enter the name of a place that corresponds to one or more geospatial locations and a species to run a model using ENM. Using this approach to synthesizing model layers, the framework can produce niche model results with a simplified user experience when compared to traditional approaches to ENM. Input layers for the model can be generated dynamically using, for example, OpenStreetMap and the spatial search functionality of Solr. Models can then be run using either user-specified or automatically determined parameters after normalizing them into a common grid. In addition, in one or more embodiments, results are visualized in a web interface, which can allow for quick validation. Model results and all surrounding metadata can also be made accessible to the user for further study.

As used herein, the term geospatial data refers to data that has explicit geographic positioning information included within it, such as a road network from a geographic information system (GIS), or a geo-referenced satellite image. One type of geospatial data is vector data which uses simple geometric objects such as points, lines, and areas (e.g., polygons) to represent geospatial locations in the geospatial data. Another type of geospatial data is raster data which uses a grid to represent its geographic information. In raster data, points, or geospatial locations, are represented by single cells, lines by sequences of neighboring cells, and areas by a collection of cells. In one or more embodiments described herein the niche model data layers are represented as raster data.

Turning now to FIG. 1, components of a flexible ENM processing framework 100 are generally shown according to one or more embodiments. The ENM framework 100 shown in FIG. 1 includes a correlation process 114 that receives datasets 116 from several sources (Source 1 and Source 2 are shown in FIG. 1). The correlation processor 114 correlates the datasets 116, and then stores the correlated datasets 116 into a document store 102. In accordance with one or more embodiments, the datasets 116 are disparate in that they have a plurality of different contents and formats, and can include, for example, geospatial referenced gridded datasets that specify values of environmental parameters for corresponding geospatial locations. Examples of sources of the datasets 116 include, but are not limited to: data from National Climatic Data Center (NCDC), National Oceanic & Atmospheric Administration (NOAA), Web Soil Survey (WSS), Global Biodiversity Information Facility (GBIF), U.S. Geological Survey (USGS), and Geofabrik. The data can be received in any format such as, but not limited to: gridded data files such as netCDF, gridded binary (GRIB) format variants, georeferenced comma-separated values (CSVs), and/or raster based formats such as GeoTIFF.

The datasets can use different terminology for geospatial locations and/or environmental parameters. As part of the correlation process 114, the different names can be connected so that they use common terminology before being stored in the semi-structured document store 102. For example, one source may refer to latitude as "lat" and another source may refer to latitude as "latitude." The correlation process 114 can include a program written by a programmer to connect "lat" and "latitude", and to refer to both as "latitude" or some other common label. The correlation process indexes the datasets 116 into annotated document structures (e.g., semi-structured documents) by aggregating data sources together. In one or more embodiments correlation is implemented by one or more code modules per data source for each of the input file formats to be supported. In each module that supports an input file type, software checks can seek out a plurality of heuristic terms dealing with geospatial location. For instance, sample terms defining equivalent geospatial concepts include the terms "lat", "latitude", and Latitude. The input files can be parsed, and during the parsing stage or upon completion of parsing those terms and associated values are recognized for those terms. At a minimum, input file parsers detect at least one coordinate/value pair for geo-referencing. Anything else that can be heuristically or mechanistically extracted as key/value pairs is optional but can be useful as annotations and indexed in the same document or a linked document containing the required geo-reference key value pair.

In cases where multiple variants of the same geospatial concept term are found within a document, they can be merged or entered with their corresponding values as separate fields in the document store. To join values from sources across document stores, the required geolocation reference can be used as the primary joining value. Since every measurement is described by either a pointwise latitude/longitude pair (or in the general case a bounding polygon to define regions with less overhead than enumerating each point within the region), spatial search can be utilized, for instance the spatial search found in Apache Solr, to find relations based on geospatial location across the other arbitrary key value pairs that were not geospatial in nature. By importing annotated data sets from OpenStreetMap, embodiments are able to define a mapping of natural language place names to the corresponding coordinates/polygons defining those locations.

In the examples described herein, the document store 102 is implemented using Apache Solr from the Apache Software Foundation, and the tool used to define a geographic region made up of geospatial locations is OpenStreetMap. OpenStreetMap data includes polygons that describe different regions, allowing these polygons to be retrieved by name. Once a polygon is retrieved, a bounding box is determined from the polygon and used to search for data for the model being generated. In one or more other embodiments, the ENM framework utilizes other tools such as, but not limited to: ArcGIS from Esri and Geospatial Data Abstraction Library (GDAL) from the Open Source Geospatial Foundation. ArcGIS is a geographic information system (GIS) for working with maps and geographic information. It can be used for: creating and using maps; compiling geographic data; analyzing mapped information; sharing and discovering geographic information; using maps and geographic information in a range of applications; and managing geographic information in a database. GDAL is a computer software library for reading and writing raster and vector geospatial data formats. As a library, it presents a single abstract data model to the calling application for all supported formats.

The document store 102 contains values of environmental parameters measuring weather related phenomena, species occurrences, human population, soil types, land cover, elevation, and OpenStreetMap data. Maps from OpenStreetMap can be combined with niche model relevant data to create models based on named geographic regions. Examples of environmental parameters, or environmental data, include, but are not limited to: mean annual temperature; mean diurnal temperature range; isothermality; temperature seasonally; maximum temperature of warmest month; minimum temperature of coldest month; temperature annual range; annual mean precipitation; precipitation of the wettest month; precipitation of the driest month; precipitation seasonally; diurnal temperature range; frost-free days; solar radiation; annual mean monthly minimum temperature; annual mean monthly maximum temperature; vapor pressure; wet days; actual and potential evapotranspiration; moisture deficit and surplus; soil moisture; normalized difference vegetation index; life zones; soil class; vegetation class; vegetation type; wetlands; world ecosystems; actual forest cover; elevation; potential vegetation; proximity to coast; species occurrence data; soil types; elevation; watersheds; lakes; and land use.

Components of a flexible ENM framework 100 shown in FIG. 1 also include an iteration process 104 for creating niche model data layers 110 (also referred to herein as niche model input layers or model layers) based on the data in the document store 102. The iteration process 104, for example, may be a top down recursion from the perspective of the food chain involving the specie of interest. For instance, a particular niche for a giant panda which may have a trivially determined food source data set given the small dietary range of the species (bamboo), will return a different volume of results if seeking a particular niche for the hooded merganser (*Lophodytes cucullatus*) where a simple food layer may not be on file. However the data store can have access to food web information including the list of species and taxa or other hierarchical ontology of consumables for that duck species. By iterating over all known species that are consumed by the top level specie of interest, a composite layer of an arbitrary "hooded merganser food source" layer can be created. To create this layer, it may be necessary to iterate down through the chain of species recursively determining their food web requirements to build this top most layer. For instance, the aforementioned ducks are known to eat small fish, aquatic insects, crustaceans (especially crayfish), amphibians, vegetation, and mollusks (their diet is broader than in other mergansers, which eat fish almost exclusively). Thus for a food existence layer, embodiments may need to determine iterations for individual availability of small fish, crayfish, aquatic insects and so on and ultimately creating a superset of those locations deemed to have food sources, weighted by the number and variety of food sources available at each location. In turn each layer may require lower layers still until direct lookup information can be achieved based on individual specie occurrence information or heuristic rules governing occurrence assumptions.

The components shown in FIG. 1 also include inference logic 118 for creating additional niche model data layers 110 based on the niche model data layers 110 created by the iteration process 104. The inference logic 118 can combine the data in two or more of the niche model data layers 110 and/or by performing a calculation on the contents of one or more of the niche model data layers 110. For example, a new niche model data layer 110 that indicates a slope around a geographical location can be created by taking a data layer 110 that indicates altitude of geographic locations and calculating a slope based on an altitude of a geographic location and surrounding geographic locations. Another example is the computation of a drainage direction map (DDM) from a digital elevation map (DEM). Known algorithms for computing a drainage direction layer from an elevation layer include: D8, MFD, Rho8, DEMON, D-Inf, and so on, with different variations within those listed. The drainage direction map may be useful directly as an input layer of drainage direction from one of the algorithms mentioned, or a further derived layer may be computed by computing the drainage directions across multiple algorithmic approaches and further deriving an ensemble "confidence" layer of flow direction based on cell-wise individual agreement across the distinct DDM layers. It should be appreciated that this approach used iterative methods from a single starting input layer to derive a plurality of derived input layers.

The inference logic 118 can also combine the contents of one or more of the niche model layers 110 with additional data from the document store or other source. For example, a new niche model data layer 110 that indicates an amount of shade in a geographic location can be inferred based on contents of a niche model data layer 110 that indicates altitude of the geographic location and surrounding locations, and on data that indicates a position of the sun. In another more sophisticated example, one may compute categorical vegetation cover based on an input data set layer comprising an annotated or cross referenced digital elevation map layer including signal strength of the measuring device at each sampled point in addition to the nominal height/depth value. For example each point may contain data about the acoustic signal return of underwater acoustic bathymetry scanning devices or laser return intensity from LiDAR based scanning equipment. This data layer can be combined with a machine learned or otherwise precomputed data set of signal strengths to vegetation type to derive a derived vegetative cover input layer. For instance, a strong signal return may indicate mosses and lichen whereas a weaker signal return may indicate shrubs or tree canopy. The extent of this identification of vegetative cover might further provide disambiguation of the vegetative type down to the species level. Analogous examples exist for underwater vegetation with nitella beds, and milfoil fields for instance.

The components in FIG. 1 also include a specie query that requests results that specify predicted geographic locations of a specie 112 based on information about the specie contained in the species data 106 and based on the data layers 110 which include environmental data.

Figure 2:
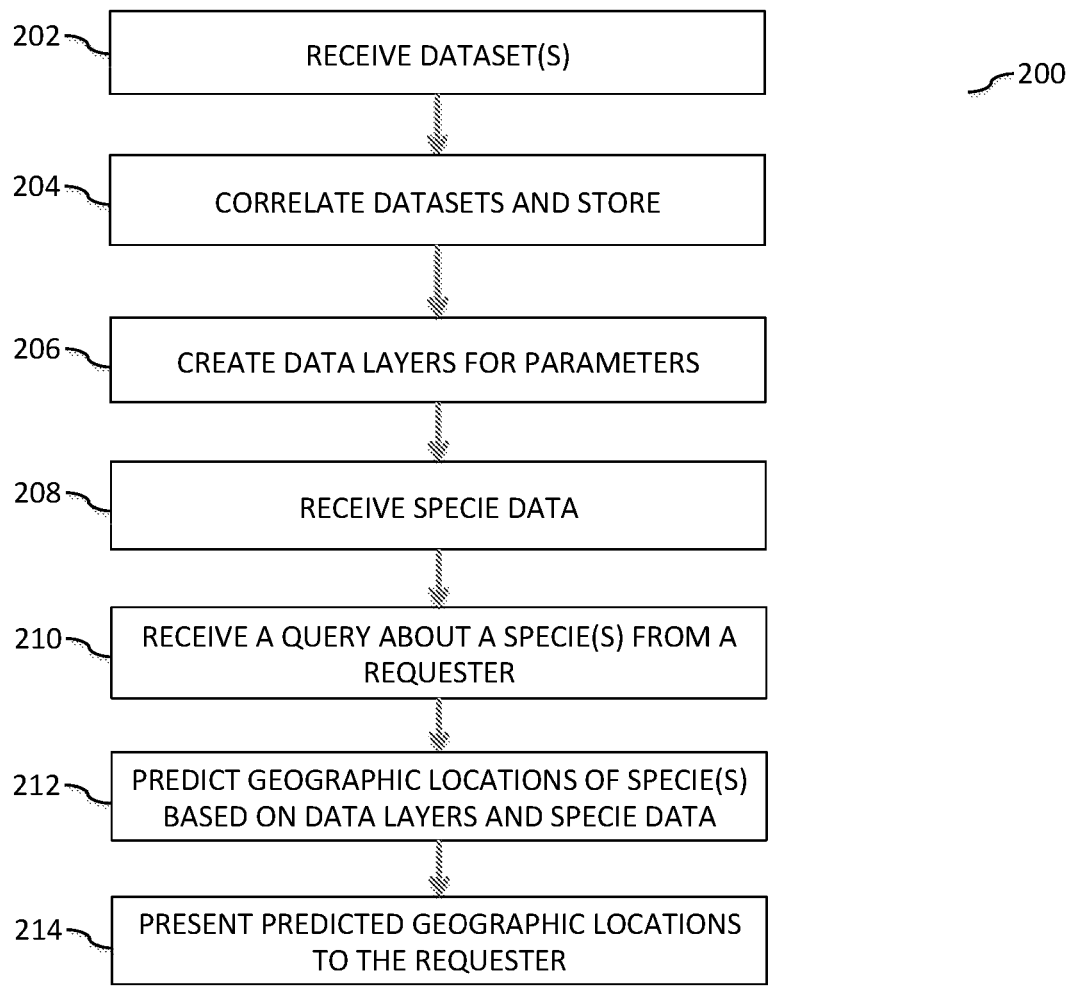
FIG. 2 illustrates a flow diagram for performing ENM in accordance with one or more embodiments.

Turning now to FIG. 2, a flow diagram 200 for performing ENM is generally shown in accordance with one or more embodiments. At block 202, datasets, such as datasets 116 in FIG. 1, are received from a variety of sources. As described previously, the datasets can be disparate datasets. At block 204, the disparate datasets are correlated and stored in a document store, such as document store 102 in FIG. 1. In one or more embodiments this can be performed by aggregating the plurality of disparate datasets into a document store with semi-structured attributes, with each document in the document store specifying attributes that include a geospatial location and a value of an environmental parameter at the geospatial location. The document is referred to as being semi-structured because it includes defined fields/attributes for the geospatial location and the value of the environmental parameter, and the rest of the document may include unstructured text or other information whose contents are not identified. The disparate datasets can include geospatial referenced gridded datasets and the aggregating can include indexing the datasets into annotated document structures to be stored in the document store. The environmental parameters can include, but are not limited to: climatological parameters having to do with climate; soil data parameters; land use parameters; and population density data parameters.

At block 206, data layers, or niche model layers, are created for the environmental parameters at the geospatial locations that are included in a specified geographic region. One layer is generated for each of the environmental parameters. In one or more embodiments, the generating includes identifying documents in the document store that contain information related to the geospatial locations and to the environmental parameter and iterating through the identified documents to determine a value of the environmental parameter at each of the geospatial locations. Also as part of the generating, a grid with cells representing the geospatial locations in the geographic area is filled in with the determined values of the corresponding environmental parameter is created, and then stored as a niche model layer for the environmental parameter.

In one or more embodiment, a niche model layer is generated for a combination of the environmental parameters and/or inferred based on contents of one or more niche model layers. For example, for layers which are continuous valued numerical measurements over some period of time, layers that indicate the minimum, mean, and maximum values over that time period can be derived. Thus, three data layers will be generated for the region of interest from a single data type.

In accordance with one or more embodiments, categorical data types use nearest neighbor interpolation for gridded data sources. For categorical data that is defined by region or polygon (i.e., the original data source was a shape), simple point-in-polygon tests can be performed for each location in the blank grid to determine what value should be assigned. The creation of a grid for each parameter, or data type, allows the easy creation of GeoTIFF input layers which can be fed into a tool based for example, on openModeller which describes a generic approach to species' potential distribution modeling. In addition, a tool such as GeoTools can be used to handle the reading and writing of various GIS file formats.

Still referring to FIG. 2, at block 208, species data that describes environmental attributes of one or more species is received. The species data can be retrieved from the document store or from another storage location. In one or more embodiments, at least some of the environmental attributes correspond to parameters in the niche model layers. For example, an attribute may be that the species thrives in geographic locations with a low population density and not in geographic locations with a high population density. These population density attributes can correspond to a niche model layer created for a population density parameter.

At block 210, a query is received that requests information about potential geospatial locations of a particular species. In one or more embodiments, in order to generate a model, a user can enter, via the query, the name of a place or a unique bounding box to specify the range of the model. In addition, the query can specify the species for which the model will be generated by entering the scientific or common name. In addition, the query can specify which input layers to use in the model creation, or let the systems make that determination. In one or more embodiments, the default is for the system to start by including all of the niche model layers and then to remove layers that appear to be very similar to one another in the specified region.

In one or more embodiments, in order to initiate model generation, a user interface can be accessed. The user can create a model by clicking on a "Generate Model" tab on a user interface screen and following the instructions. The user interface can prompt the user to fill in three form fields in order to create the model: a first text field asking for the user to enter the name of a location of interest for the model (this area determines the bounding box which the model is projected onto); a second text field that prompts the user for the name of the species in question (and can auto-complete both scientific and common names which will provide the string that is used in the database query for occurrences; and a checkbox field that allows the user to select which layers are relevant to the niche model for the given species.

In one or more embodiments blocks 206 and 208 are performed after block 210 and only for the requested specie and geographic region specified by the query in block 210.

At block 212, the future geospatial location of the species is predicted based on environmental attributes of the species and contents of the niche model layers. In one or more embodiments, the predicting includes generating a composite grid with cells representing the geospatial locations. The composite grid can be generated by using niche model layers as a set of filters for ruling out potential geospatial locations represented by cells in the grid. Once the user has entered the information described above in reference to block 210, model creation begins at block 212. In one or more embodiments, the relevant data are queried and both data and occurrence points that exist inside the bounding box of the region are determined. From these returned data, the highest resolution dataset can be determined. This highest resolution grid can be set as the common grid to which all layers will be normalized. In one or more embodiments, normalization is performed by generating a blank grid for each data type and then interpolating, from the original data points, the values of each point on the blank grid. For weather related variables, Barne's interpolation can be used, while for other types of environmental data a simple bi-linear interpolation can be used.

In accordance with one or more embodiments, once the user has input the parameters for model creation, a bounding box is generated for the named region by resolving the input to the corresponding OpenStreetMap polygon, and taking the upper right and lower left corners from this polygon. Data layer and occurrence data can then be retrieved from Solr based on this bounding box. At this stage, derived layers can be computed by taking a transform of the original data, (e.g., the maximum value recorded at a geospatial location). Data layers with naturally low resolution can be interpolated to match those with higher resolution. In one or more embodiments, the layer data is fed through an algorithm relying on Geotools to create geoTIFFs which can later be used for model generation. An occurrence file can also be created at this point to be fed into the openModeller tool.

Once the layers and occurrence files have been generated, a request file is written and submitted to openModeller to generate the model. The openModeller tool can project the niche model into a TIFF formatted file.

At block 214, the predicted geographic locations are output to the requestor. In one or more embodiments, the results are overlaid on top of a geographic map. In one or more embodiments, the grid with the results is output with an indicator of the geographic region covered by the results.

In addition, the individual data layers, represented as gridded datasets or in raster format, can also be output to the requestor along with model statistics. Model statics can include statistics for training data such as threshold, accuracy, omission error percentage, as well as projection statistics such as the number of grid cells where occurrence is predicted as a percentage of the geographic region displayed, and the number of cells contained in the model underlying the output visualization.

The model projection, species occurrence data, and statistical output of openModeller can all be displayed in an interactive interface. This display portal can project the model over an OpenStreetMap instance with OpenLayers, and also display the data layers used to generate the model, along with the model statistics.

Figure 3:
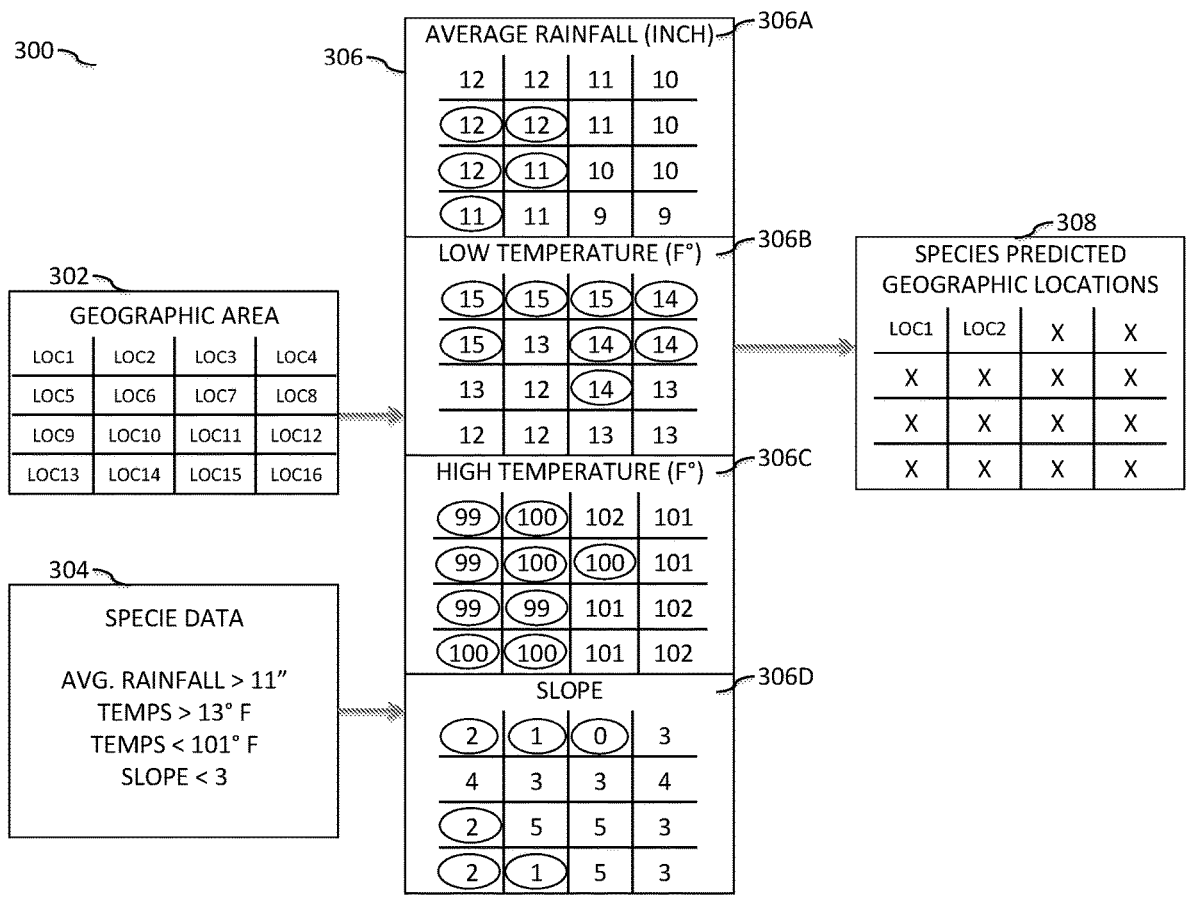
FIG. 3 illustrates a block diagram of data layers used in ENM in accordance with one or more embodiments.

Turning now to FIG. 3, a block diagram 300 of data layers used in ENM are generally shown in accordance with one or more embodiments. The block diagram 300 shown in FIG. 3 illustrates a simplified example for explanatory purposes. FIG. 3 depicts a grid of a geographic area 302 and specie data 304. In one or more embodiments, the grid of the geographic area represents sixteen geospatial locations, which together make up the geographic region that a user has requested be modeled. Each of the locations in the geographic area corresponds to a cell in the data layers 306 and the cells are of uniform size. Thus, the cell in the upper left corner of the average rainfall data layer 306A corresponds to "LOC 1" in the geographic area, that is, the average rainfall in the geospatial location "LOC 1" is 12 inches. Similarly, based on contents of the upper left corner of the low temperature data layer 306B, the low temperature at geospatial location "LOC 1" is 15 degrees Fahrenheit; based on contents of the upper left corner of the high temperature data layer 306C, the high temperature at geospatial location "LOC 1" is 99 degrees Fahrenheit; and based on contents of the upper left corner of the slope type data layer 306D, the slope at geospatial location "LOC 1" is "2" (which for example, can correspond to a slope having an angle of 20% or to some other slope specified in a look up table).

In the example shown in FIG. 3, the specie attributes that are available include average rainfall, high temperature, low temperature, and slope. These attributes can be input via a user query or they can be obtained from previously collected species data. The data layers used in the example shown in FIG. 3 describe values of the environmental parameters that correspond to the attributes available about the species. In one or more embodiments a filtering technique is performed to output a grid containing predicted geographic locations 308 (which correspond to the locations in the grid showing the geographic area 302) of the species. The locations circled in the grids in the data layers 306 indicate environmental parameter values that meet the criteria specified by the specie data 304. The only two locations where all four environmental parameters meet the criteria are "LOC 1" and "LOC 2", and thus these are the predicted future locations of the specie. In one or more embodiments, the grid containing predicted geographic locations 308 is output to a user interface device such as a display screen along with a key that describes the geospatial locations represented by the grid. In one or more embodiments, the data is overlaid on a geographic map. In addition, the data layers 306 and specie data 304 used to generate the model can be output to a user.

Figure 4:
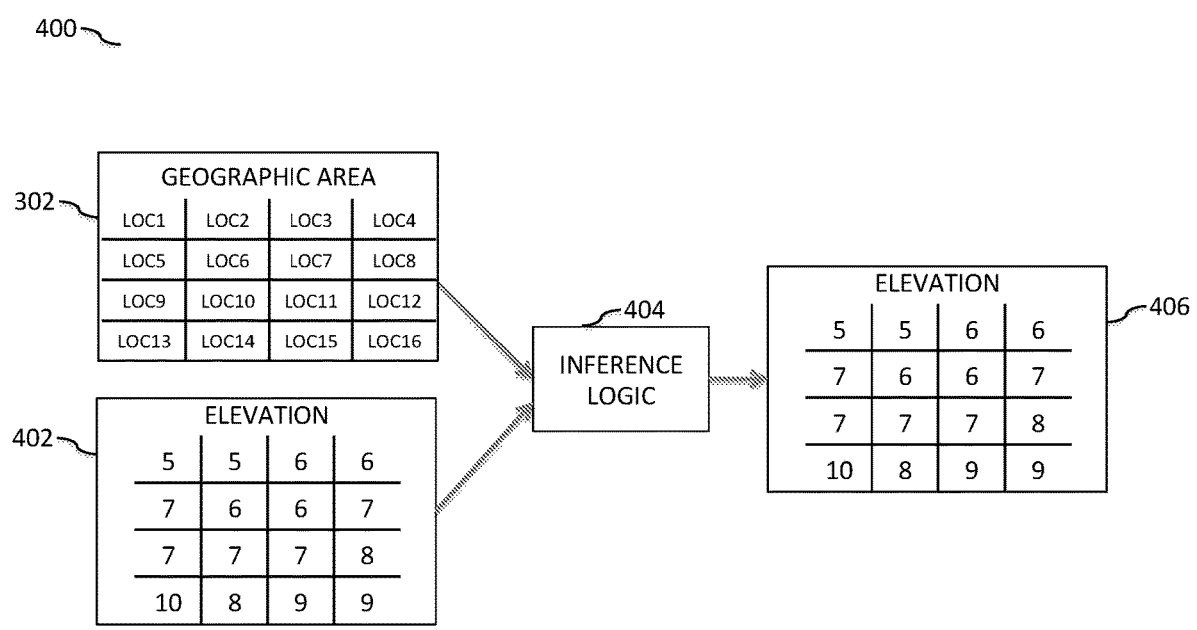
FIG. 4 illustrates a block diagram of inferring a slope data layer in accordance with one or more embodiments.

Turning now to FIG. 4, a block diagram 400 of inferring a slope data layer is generally shown in accordance with one or more embodiments. The block diagram 400 shown in FIG. 4 illustrates a simplified example for explanatory purposes. FIG. 4 depicts a grid of a geographic area 302 and an elevation data layer 402 with elevation, or altitude data corresponding to the geographic locations in the grid of the geographic area 302. The slope data layer 406 is inferred by the inference logic 404 based on contents of the elevation data layer 402. Slope may be an important predictor, alone or in combination with other data, of species as particular species may not be able to thrive in locations with extreme slopes. The slope is calculated in the slope data layer 406 as the largest elevation difference between the geographic location and its eight neighboring geographic locations. This is just one method of determining slope and other algorithms can also be implemented.

Figure 5:
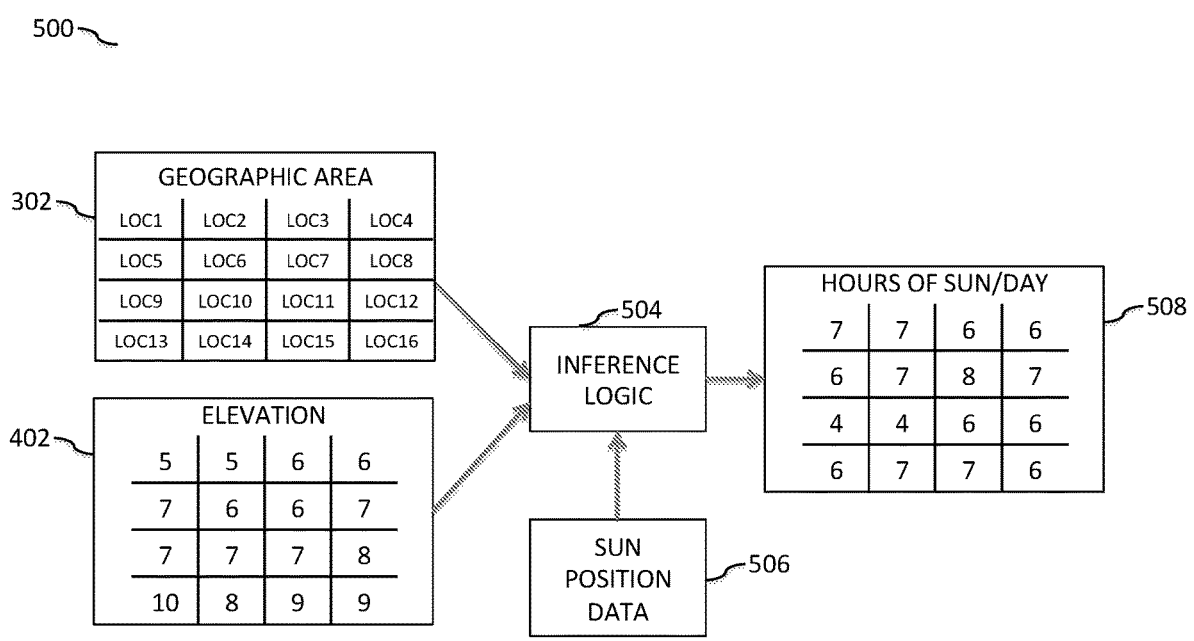
FIG. 5 illustrates a block diagram of inferring a shade data layer in accordance with one or more embodiments.

Turning now to FIG. 5, a block diagram 500 of inferring a shade data layer is generally shown in accordance with one or more embodiments. The block diagram 500 shown in FIG. 5 illustrates a simplified example for explanatory purposes. FIG. 5 depicts a grid of a geographic area 302 and an elevation data layer 402 with elevation, or altitude data corresponding to the geographic locations in the grid of the geographic area 302. The hours of sun/day data layer 508 is inferred by the inference logic 504 based on contents of the elevation data layer 402 and contents of sun position data 506. In another embodiment, a data layer is inferred for each hour (or other increment) of a day to indicate whether the geographic location is sunny or shady at that particular time. This data can be used individually or rolled up into the hours of sun/day data layer 508 shown in FIG. 5.

In accordance with one or more embodiments, in order to avoid generating models with the same input parameters repeatedly, models are stored in the framework for search later on. Parameters used as input, along with output images, statistics, and metadata can all be stored in Solr, and then presented to a model creator either via a search mechanism, or automatically during model creation if the input parameters to a new model closely match an existing model. This can save a user time, allow for easy comparison of already generated models, and over time allow users to access a breadth of models for varying species and locations.

One or more embodiments can be utilized to create a threat model which includes not only the potential distribution of a single species, but many potential invaders which could cause harm to the environment. Models can be computed for many potential invasive species, and each ranked according to the suitability of the environment in question for that species. Since the data architecture lends itself to parallelization, it is possible to run many models in parallel to speed up such a computationally difficult task.

Figure 6:
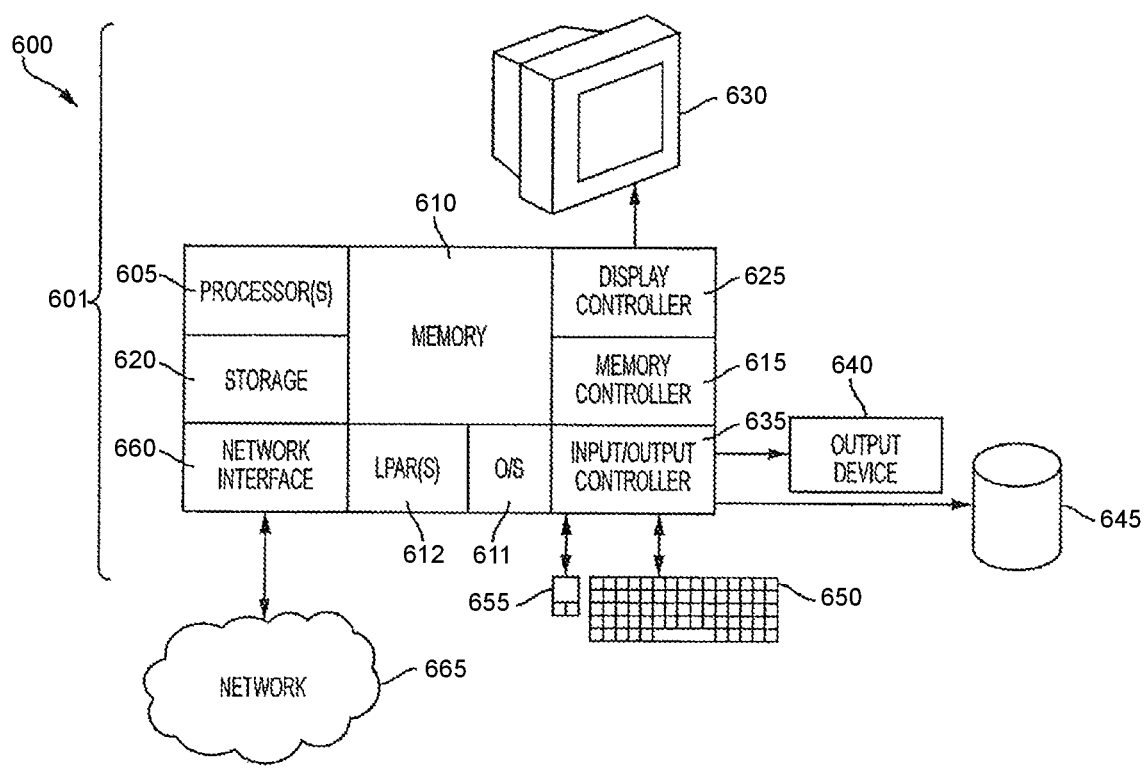
FIG. 6 illustrates a computer system for performing ENM in accordance with one or more embodiments.

Turning now to FIG. 6, a computer system for ENM is generally shown according to one or more embodiments. The methods described herein can be implemented in hardware, software (e.g., firmware), or a combination thereof. In an exemplary embodiment, the methods described herein are implemented in hardware as part of the microprocessor of a special or general-purpose digital computer, such as a personal computer, workstation, minicomputer, or mainframe computer. The system 600 therefore may include general-purpose computer or mainframe 601 capable of running multiple instances of an O/S simultaneously.

In an exemplary embodiment, in terms of hardware architecture, as shown in FIG. 6, the computer 601 includes one or more processors 605, memory 610 coupled to a memory controller 615, and one or more input and/or output (I/O) devices 640, 645 (or peripherals) that are communicatively coupled via a local input/output controller 635. The input/output controller 635 can be, for example but not limited to, one or more buses or other wired or wireless connections, as is known in the art. The input/output controller 635 may have additional elements, which are omitted for simplicity, such as controllers, buffers (caches), drivers, repeaters, and receivers, to enable communications. Further, the local interface may include address, control, and/or data connections to enable appropriate communications among the aforementioned components. The input/output controller 635 may include a plurality of sub-channels configured to access the output devices 640 and 645. The sub-channels may include fiber-optic communications ports.

The processor 605 is a hardware device for executing software, particularly that stored in storage 620, such as cache storage, or memory 610. The processor 605 can be any custom made or commercially available processor, a central processing unit (CPU), an auxiliary processor among several processors associated with the computer 601, a semiconductor based microprocessor (in the form of a microchip or chip set), a macroprocessor, or generally any device for executing instructions.

The memory 610 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 610 may incorporate electronic, magnetic, optical, and/or other types of storage media. Note that the memory 610 can have a distributed architecture, where various components are situated remote from one another, but can be accessed by the processor 605.

The instructions in memory 610 may include one or more separate programs, each of which comprises an ordered listing of executable instructions for implementing logical functions. In the example of FIG. 6, the instructions in the memory 610 a suitable operating system (OS) 611. The operating system 611 essentially controls the execution of other computer programs and provides scheduling, input-output control, file and data management, memory management, and communication control and related services. In accordance with one or more embodiments, the memory 610 and/or an I/O device 645 can be used to store the document store 102 and the species data 106 described herein.

The memory 610 may include multiple logical partitions (LPARs) 612, each running an instance of an operating system. The LPARs 612 may be managed by a hypervisor, which may be a program stored in memory 610 and executed by the processor 605.

In an exemplary embodiment, a conventional keyboard 650 and mouse 655 can be coupled to the input/output controller 635. Other output devices such as the I/O devices 640, 645 may include input devices, for example but not limited to a printer, a scanner, microphone, and the like. Finally, the I/O devices 640, 645 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 600 can further include a display controller 625 coupled to a display 630. In an exemplary embodiment, the system 600 can further include a network interface 660 for coupling to a network 665. The network 665 can be an IP-based network for communication between the computer 601 and any external server, client and the like via a broadband connection. The network 665 transmits and receives data between the computer 601 and external systems. In an exemplary embodiment, network 665 can be a managed IP network administered by a service provider. The network 665 may be implemented in a wireless fashion, e.g., using wireless protocols and technologies, such as WiFi, WiMax, etc. The network 665 can also be a packet-switched network such as a local area network, wide area network, metropolitan area network, Internet network, or other similar type of network environment. The network 665 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 601 is a PC, workstation, intelligent device or the like, the instructions in the memory 610 may further include a basic input output system (BIOS) (omitted for simplicity). The BIOS is a set of essential software routines that initialize and test hardware at startup, start the OS 611, and support the transfer of data among the hardware devices. The BIOS is stored in ROM so that the BIOS can be executed when the computer 601 is activated.

When the computer 601 is in operation, the processor 605 is configured to execute instructions stored within the memory 610, to communicate data to and from the memory 610, and to generally control operations of the computer 601 pursuant to the instructions.

In accordance with one or more embodiments described herein, data layers are generated automatically for a given niche model, and layer generation can be determined automatically or based on user input. In addition, metadata for the created input layers can be easily tracked. For example, the source of the layer's encapsulating dataset, the date it was updated, and the spatial resolution can all be tracked.

In accordance with one or more embodiments, the flexible framework described herein is easy to use and allows for multiple, rapid iterations of model creation and validation. The data collection and management burden can be completely removed from the end-user who wishes to run the models. Further, the efficiency of the data architecture can allow the flexible framework to scale well with both the extent of the models being generated, and the number of models being run. Model runs can be parallelized, so that several different algorithms can be run at once, and the final model can be a blend of these individual model runs.

In accordance with one or more embodiments, the data stored in the architecture is high resolution, broad geographic coverage, accurate, and relevant to ENM creation. This allows for comprehensive aggregated datasets to be used by the flexible framework to generate niche model.

In accordance with one or more embodiments, the flexible framework allows for easy storage of an end users custom data. Data importers can be written for many different file formats often used in geographic information systems (GIS) applications, including but not limited to: GeoTIFF; Shapefiles; ESRI ArcGrid; Erdas Imagine; OpenStreetMap XML; and comma-separated values (CSV) files.

In accordance with one or more embodiments, the flexible framework derives relevant data layers from types of data selected for use in a given model, which can improve model accuracy. In certain cases, these derived layers can be of greater importance to model accuracy than including new, different types of layers. For example, including average mean temperature can be more important to model accuracy than the number of layers used.

In accordance with one or more embodiments, an interface of the flexible framework allows for easy statistical validation of models, as well as quick visual testing of input layers and model output. Model output can be overlaid on an interactive map, allowing local biologists to visually inspect and confirm a model's validity.

In an exemplary embodiment, the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
    aggregating a plurality of datasets having different contents and different formats into a document store, wherein each document in the document store is a semi-structured document specifying a geospatial location and a value of an environmental parameter at the geospatial location, the document store comprising a plurality of documents specifying a plurality of different geospatial locations and a plurality of different environmental parameters, the environmental parameters including a climatological parameter;
    generating niche model layers for the environmental parameters at the geospatial locations based on contents of the document store, the niche model layers including a model layer for each of the different environmental parameters;
    creating an additional niche model layer for a derived environmental parameter at the geospatial locations, the derived environmental parameter not included in the plurality of different environmental parameters and the creating based at least in part on one of the previously generated niche model layers;
    predicting a future geospatial location of a species based on environmental attributes of the species and contents of at least a subset of the niche model layers, the subset including the additional niche model layer; and
    outputting the predicted future geospatial location of the species overlaid on a geographic map.

2. The method of claim 1, wherein the predicting comprises generating a composite grid with cells representing the geospatial locations, the generating including using the at least a subset of the niche model layers as a set of filters for ruling out a geospatial location as a future geospatial location of the species.

3. The method of claim 1, wherein the predicting is in response to a query from a requestor and the outputting is to the requestor.

4. The method of claim 3, wherein the generating niche model layers is in response to the query and niche model layers are generated only for parameters corresponding to attributes of the species.

5. The method of claim 3, wherein the query specifies a geographic region which is made up of a plurality of geospatial locations and the geospatial locations in the niche model layers are selected based on the geographic region.

6. The method of claim 1, wherein the document store further comprises species data including the environmental attributes of the species.

7. The method of claim 1, further comprising generating a niche model layer for a combination of the environmental parameters.

8. The method of claim 1, wherein the generating comprises, for each of the different environmental parameters:
    identifying documents in the document store that contain information related to the geospatial locations and to the environmental parameter;
    iterating through the identified documents to determine a value of the environmental parameter at each of the geospatial locations;
    creating a grid with cells representing the geospatial locations and corresponding determined values of the environmental parameter; and
    storing the grid as a niche model layer for the environmental parameter.

9. The method of claim 1, wherein the environmental parameters further include a type of parameter selected from the group consisting of soil data parameters, land use parameters, and population density data parameters.

10. The method of claim 1, wherein the datasets are geospatial referenced gridded datasets and the aggregating comprises indexing the datasets into annotated document structures to be stored in the document store.

11. The method of claim 1, further comprising outputting a gridded dataset or raster representation of at least one of the niche model layers.

12. A system comprising:
    a memory having computer readable instructions; and
    a processor for executing the computer readable instructions, the computer readable instructions including:
        aggregating a plurality of datasets having different contents and different formats into a document store, wherein each document in the document store is a semi-structured document specifying a geospatial location and a value of an environmental parameter at the geospatial location, the document store comprising a plurality of documents specifying a plurality of different geospatial locations and a plurality of different environmental parameters, the environmental parameters including a climatological parameter;

generating niche model layers for the environmental parameters at the geospatial locations based on contents of the document store, the niche model layers including a model layer for each of the different environmental parameters;

creating an additional niche model layer for a derived environmental parameter at the geospatial locations, the derived environmental parameter not included in the plurality of different environmental parameters and the creating based at least in part on one of the previously generated niche model layers;

predicting a future geospatial location of a species based on environmental attributes of the species and contents of at least a subset of the niche model layers, the subset including the additional niche model layer; and outputting the predicted future geospatial location of the species overlaid on a geographic map.

13. The system of claim 12, wherein the predicting comprises generating a composite grid with cells representing the geospatial locations, the generating including using the at least a subset of the niche model layers as a set of filters for ruling out a geospatial location as a future geospatial location of the species.

14. The system of claim 12, wherein the predicting is in response to a query from a requestor and the outputting is to the requestor.

15. The system of claim 12, wherein the instructions further include generating a niche model layer for a combination of the environmental parameters.

16. The system of claim 12, wherein the generating comprises, for each of the different environmental parameters:

identifying documents in the document store that contain information related to the geospatial locations and to the environmental parameter;

iterating through the identified documents to determine a value of the environmental parameter at each of the geospatial locations;

creating a grid with cells representing the geospatial locations and corresponding determined values of the environmental parameter; and storing the grid as a niche model layer for the environmental parameter.

17. The system of claim 12, wherein the datasets are geospatial referenced gridded datasets and the aggregating comprises indexing the datasets into annotated document structures to be stored in the document store.

18. A computer program product comprising a computer readable storage medium having program instructions embodied therewith, the program instructions executable by processing circuitry to cause the processing circuitry to perform:

aggregating a plurality of datasets having different contents and different formats into a document store, wherein each document in the document store is a semi-structured document specifying a geospatial location and a value of an environmental parameter at the geospatial location, the document store comprising a plurality of documents specifying a plurality of different geospatial locations and a plurality of different environmental parameters, the environmental parameters including a climatological parameter;

generating niche model layers for the environmental parameters at the geospatial locations based on contents of the document store, the niche model layers including a model layer for each of the different environmental parameters;

creating an additional niche model layer for a derived environmental parameter at the geospatial locations, the derived environmental parameter not included in the plurality of different environmental parameters and the creating based at least in part on one of the previously generated niche model layers;

predicting a future geospatial location of a species based on environmental attributes of the species and contents of at least a subset of the niche model layers, the subset including the additional niche model layer; and outputting the predicted future geospatial location of the species overlaid on a geographic map.

19. The computer program product of claim 18, wherein the predicting comprises generating a composite grid with cells representing the geospatial locations, the generating including using at least a subset of the niche model layers as a set of filters for ruling out a geospatial location as a future geospatial location of the species.

20. The computer program product of claim 18, wherein the instructions further include generating a niche model layer for a combination of the environmental parameters.

* * * * *